(12) United States Patent
Smith

(10) Patent No.: US 10,842,665 B2
(45) Date of Patent: Nov. 24, 2020

(54) TRIGGERING THE AUTONOMIC NERVOUS SYSTEM

(71) Applicant: David Smith, Richmond, IN (US)

(72) Inventor: David Smith, Richmond, IN (US)

( * ) Notice: Subject to any disclaimer, the term of this patent is extended or adjusted under 35 U.S.C. 154(b) by 33 days.

(21) Appl. No.: 16/279,607

(22) Filed: Feb. 19, 2019

(65) Prior Publication Data

US 2019/0175389 A1 Jun. 13, 2019

Related U.S. Application Data

(62) Division of application No. 15/138,306, filed on Apr. 26, 2016, now Pat. No. 10,245,176.

(60) Provisional application No. 62/152,993, filed on Apr. 27, 2015.

(51) Int. Cl.
*A61F 7/00* (2006.01)
*A61N 1/36* (2006.01)

(52) U.S. Cl.
CPC .......... *A61F 7/007* (2013.01); *A61N 1/36031* (2017.08); *A61F 2007/0003* (2013.01); *A61F 2007/0006* (2013.01); *A61F 2007/0017* (2013.01); *A61F 2007/0075* (2013.01); *A61F 2007/0086* (2013.01)

(58) Field of Classification Search
CPC ...... A61F 2007/0003; A61F 2007/0004; A61F 2007/0006; A61F 2007/0007; A61F 2007/0017; A61F 2007/0075; A61F 2007/0086; A61F 7/07; A61N 1/36014; A61N 1/0452; A61N 1/0456
See application file for complete search history.

(56) References Cited

U.S. PATENT DOCUMENTS

| | | | |
|---|---|---|---|
| 6,840,955 B2* | 1/2005 | Ein | A61N 1/32 607/108 |
| 2006/0064140 A1 | 3/2006 | Whitehurst et al. | |
| 2014/0081353 A1 | 3/2014 | Cook et al. | |
| 2016/0184585 A1* | 6/2016 | Kealey | A61N 1/36034 607/45 |
| 2018/0056065 A1* | 3/2018 | Muller | A61N 1/0456 |

* cited by examiner

*Primary Examiner* — Paula J Stice
(74) *Attorney, Agent, or Firm* — Maginot, Moore & Beck, LLP

(57) ABSTRACT

A device and method is provided for treating a person by providing controlled stimulation of a branch of the trigeminal nerve of the person to induce a dive reflex response in the person. A device for providing this treatment includes a stimulus component controllably operable to stimulate a branch of the trigeminal nerve of a person. The stimulus component can be a Peltier device configured to reduce the temperature of the person's face in proximity to a branch of the trigeminal nerve to induce the dive reflex. A controller controls activation of the stimulus component when it is desirable to induce the dive reflex response in the person. The controller can sense physiological and ambient conditions and can activate and deactivate the stimulus component in response to a condition falling within or outside a threshold value.

17 Claims, 4 Drawing Sheets

TRIGGERING THE AUTONOMIC NERVOUS SYSTEM

REFERENCE TO RELATED APPLICATION

This application is a divisional of and claims priority to U.S. application Ser. No. 15/138,306, filed on Apr. 26, 2016, which is a non-provisional filing of and claims priority to provisional application No. 62/152,993, filed on Apr. 27, 2015, the entire disclosure of which is incorporated herein by reference.

BACKGROUND

The present invention relates to medical devices and methods of using same, and more particularly to devices and methods for producing bradycardia, increased systemic vascular resistance, decreased cardiac work, and increased cerebral blood flow through the autonomic nervous system in the animal or human body.

The dive reflex, also known as the dive response, is the mechanism through which the human body defends itself from hypothermia and resulting death when submerged in cold water. The reflex is most graphically illustrated by the resuscitation of children, who have been submersed in farm ponds during the winter for periods exceeding the three-minute brain-death criterion. During the dive reflex, the body, through selective vasoconstriction, isolates those tissues with extended anaerobic capability from those with relatively little anaerobic capability, such as the heart and brain. Consequently, circulation to the extremities is greatly diminished, while circulation to the brain and heart continues at generally adequate or increased levels. Additionally, the pulse-rate slows and a relatively constant blood pressure is maintained. Typically, the resulting minimum dive-reflex pulse-rate is approximately 60 to 70 percent of the quiescent rate. By shunting blood to the brain and heart, and slowing the pulse-rate, the body is able to supply the required oxygen to both the brain and the heart for extended periods of cold water submersion.

Although the dive reflex phenomenon has been known for years, there are several new triggering mechanisms for the dive reflex which have only recently been determined. Through selective anatomical immersion, it has been determined that the receptor mechanism is located in the face. See, J. Finley et al, Autonomic Pathways Responsible for Bradycardia on Facial Immersion, Journal of Applied Physiology, Volume 47(6), Pages 1218-22 (December 1979). In a 1984, Moore implied in U.S. Pat. No. 4,466,439, that the dive reflex was best triggered by isolating and stimulating the seventh cranial facial nerve (Cranial Nerve VII) based on a hypothesis that the triggering receptor was in the facial nerve which surfaces at the cheeks, forward of the ears to the nose. This has now been disproved and it has since been shown that it is the completely separate cranial nerve (fifth cranial nerve V), namely the trigeminal nerve, which possesses the receptors to activate the dive response. The trigeminal nerve surfaces over the forehead, between the eyes and down the upper part of the nose. These receptors in the skin have been isolated and have been named "cold and menthol" receptors after the stimulus known (at that time) to activate them. Particularly, it is the ophthalmic division of the trigeminal nerve which carries this reflex. Further investigations have pointed to the anterior ethmoidal nerve (surfacing on the nose) as being the most capable branch to evoke this reflex.

Stimulation of the dive response causes bradycardia, reduced cardiac work, and peripheral vasoconstriction of blood vessels. Blood is removed from the limbs and all organs except the heart and the brain allowing the mammal to conserve oxygen, and shunt blood back to the heart and brain. In humans, the mammalian dive reflex is not induced when any limbs are introduced to cold water. Notably, the greatest bradycardia effect is induced when the subject is holding one's breath (which may trigger other mechanoreceptors in the lungs) with the face submerged. This finding may be particularly helpful when utilizing the dive reflex to increase G-force tolerance of military pilots or astronauts. Protocols for the military already include "breath-hold" maneuvers to increase intra-thoracic pressure (COMBAT EDGE). Further, controversy exists over whether present technologies such as ATAGS (advanced tactical anti G suits) are of any benefit in improving G force tolerance. Like MAST trousers (now all but obsolete), ATAGS attempts to push fluid and pressure from the lower extremities into the central vascular tree in an attempt to increase systemic vascular resistance, but no increase in systemic vascular resistance can be documented. Triggering the dive reflex affords the ability to directly access the autonomic nervous system and increase the vascular resistance of every non-essential vessel throughout the body. Systemic vascular resistance increases of 25% have been noted, while increases in the cerebral blood blow in humans were seen to increase by 14%.

Interestingly, it has also been demonstrated that the spleen, in humans, contracts up to 20% during this reflex to infuse blood and increase the hematocrit up to 5%, thus further improving oxygen delivery to essential central organs. This "auto transfusion" of 5% of oxygen carrying capacity becomes critical in settings where the individual is losing blood or going into shock. Naturally, with improved hemodynamics and greater oxygen delivery, cardiac work would be expected to drop and in fact this was demonstrated by this investigator to drop by at least 11% using an external monitoring device called impedance plethysmosgraphy (Bio Z monitor).

The present approach to altering the oxygen supply/demand for the heart and brain is to use the 110-year-old technology of a sublingual nitroglycerine tablet or spray that attempts to create the same scenario through chemical means. Nitroglycerine works by a mechanism of producing nitric acid inside the vascular wall (thereby dilating it), and it requires a process of absorption of the chemical (usually through the tongue) taking at least 2 minutes and lasting only 30 minutes. Further, the intent of nitroglycerin action is to improve the oxygen supply and demand curve of the heart, a goal that is completely in accord with the actions of the dive reflex. Unfortunately, nitroglycerine has not been able to demonstrate a benefit in the setting of brain attacks (strokes and transient ischemic attacks), whereas, the dive reflex should significantly prevent or at least improve tolerance of ischemia in the central circulation of the brain based on studies which have shown up to a 14% increase in flow to the cerebrum when triggering the dive reflex in humans.

As reported in the Mar. 7, 2002 issue of Nature, McKemy, Neuhausser & Julius characterized and cloned a menthol receptor from trigeminal sensory neurons that is also activated by thermal stimuli in the cool to cold range. This cold- and menthol-sensitive receptor, CMR1, is a member of the TRP family of excitatory ion channels. They proposed that CMR1 functions as a transducer of cold stimuli in the somatosensory system. In February 2004, H-J Behrendt, et.

al., published a study on the effects of 70 odorants and menthol-related substances on recombinant cold-menthol receptor TRPM8 (mTRPM8), expressed in HEK293 cells. Ten substances (linalool, geraniol, hydroxycitronellal, WS-3, WS-23, FrescolatMGA, FrescolatML, PMD38, CoolactP and Cooling Agent 10) were found to be agonists.

SUMMARY

The present invention is based on inducing the dive reflex in a controlled environment in order to specifically alleviate the considerable workload of the heart under certain conditions, such as during post-infarction convalescent periods, or even during angina events. This approach does not require the use of sublingual nitroglycerine administration. Such a pulse-rate reduction, under constant blood pressure (and improved cardiac and cerebral blood flow), would facilitate the recovery of patients due to the reduced requirement for oxygen by the heart. Additionally, because the blood supply to the extremities is greatly reduced during dive reflex through vasoconstriction, artificial inducement of the phenomenon could also be used to reduce traumatic bleeding in the extremities (and lessen shock). Moreover, since blood flow is potentiated to the brain, G-induced loss of consciousness (G-loc) in air warriors and astronauts (as well as altered level of consciousness, A-loc) can be minimized. Lastly, certain conditions can lead to orthostatic hypotension including advanced age, surgical interventions (such as post cardiotomy) and medication use. This mechanism may prevent, or at least improve tolerance and prognosis of, non-hemorrhagic brain attacks, such as strokes and TIA's. Triggering the dive reflex on demand in these settings would naturally improve the risks associated with each of the above.

The present invention thus provides a device and method for inducing the dive reflex without the inconvenience of immersing the face in cold water. The device includes a trigeminal nerve-engaging component, a mounting component for mounting the trigeminal nerve-engaging component on a person's forehead and nose, more particularly over a portion of the area where the trigeminal nerve surfaces, and a controller operable to control the activation of the trigeminal nerve-engaging component in a range sufficiently to induce the dive reflex through the application of stimulus to the trigeminal nerve. The method includes the steps of providing a device having a stimulus-controllable trigeminal nerve-engaging means, mounting the device on the trigeminal nerve distribution of a person with the trigeminal nerve-engaging means covering a portion of the area where the trigeminal nerve surfaces, and controlling the stimulus of the trigeminal nerve-engaging means in a range sufficient to induce the dive reflex.

The device and method of the present invention have several medical applications. First, the workload on the heart may be reduced by inducing the dive reflex, and associated bradycardia in that patient. Such induced bradycardia is especially beneficial to post-infarction patients, and those who may be bradycardial drug resistant. Second, traumatic bleeding in the extremities may be reduced by inducing dive reflex, due to the fact that the associated vasoconstriction reduces the volume of blood circulated through the limbs. Potentiation of cerebral blood flow is of particular importance in settings like G-induced loss of consciousness or altered consciousness, and Brain Attacks (strokes and TIA's).

These and other objects, advantages, and features of the invention will be more readily understood and appreciated by reference to the written specification and appended drawings.

DETAILED DESCRIPTION

Figure 1:
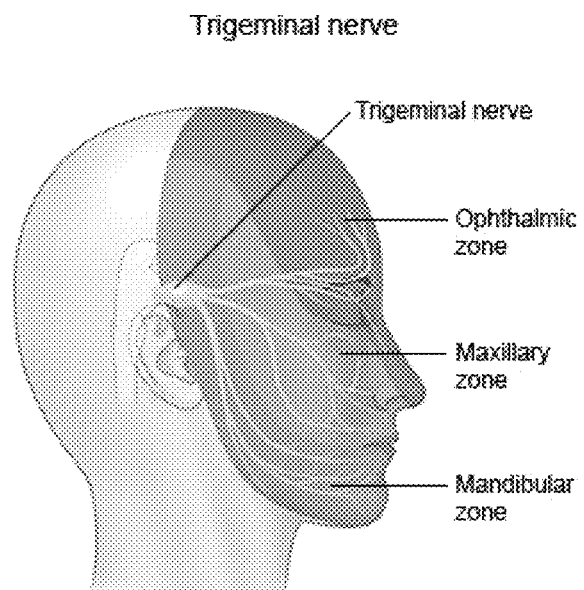
FIG. 1 is a depiction of the cutaneous distribution of the trigeminal nerve in a human.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains The portions of the ophthalmic distribution of the human trigeminal nerve that are capable of triggering the parasympathetic nervous system pertinent to dive reflex are illustrated in FIG. 1. By way of orientation, the top portion of the diagram illustrates the ophthalmic brand which includes the entire forehead and top of the cranium, the eyes, part of the temples, the bridge of the nose and down to the tip of the nose. It is this portion of the trigeminal nerve that is of most interest in stimulating the dive response.

Figure 2:
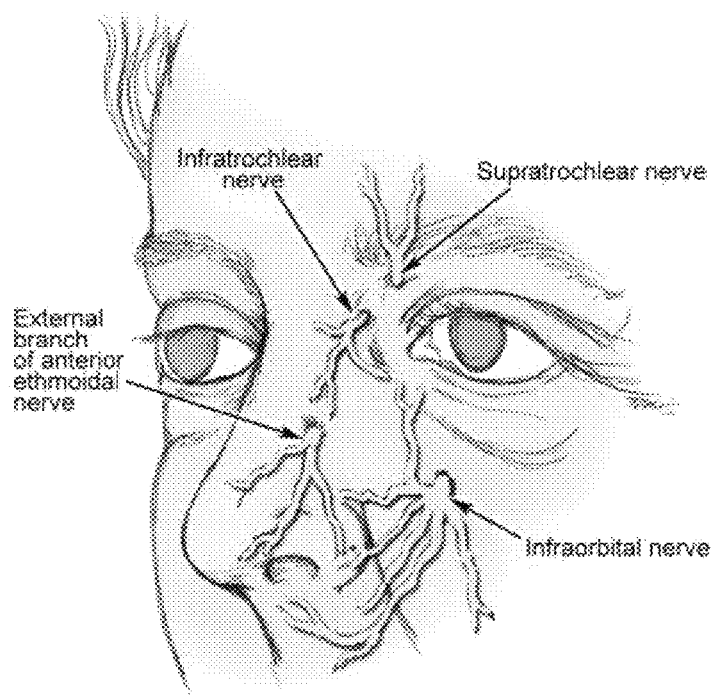
FIG. 2 is a depiction of the anterior ethmoidal nerve of the trigeminal nerve.
Figure 3:
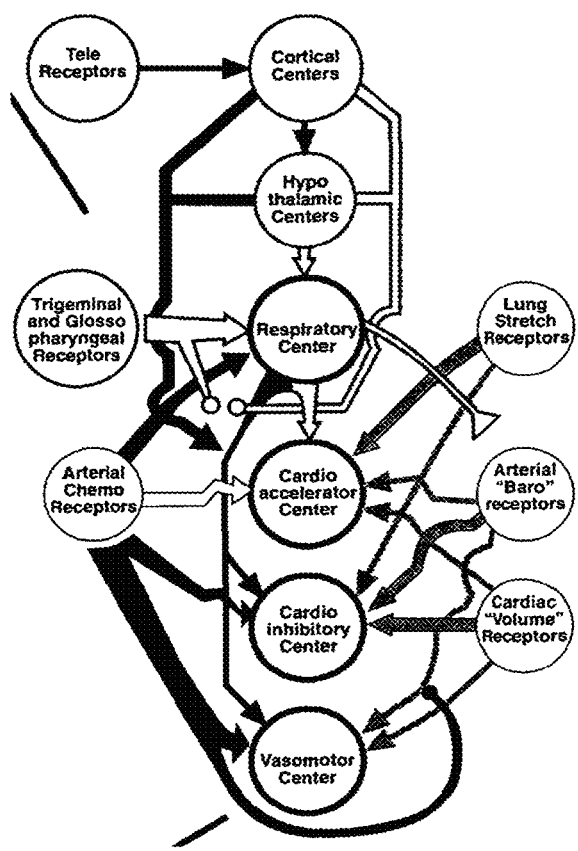
FIG. 3 is a depiction of the reflex pathway for the Mammalian dive reflex as it interacts with the autonomic nervous system.

More specifically, the anterior ethmoidal nerve branch is believed to elicit the mammalian dive reflex stronger than in the other trigeminal branches. As shown in the diagram of FIG. 2, the ethmoidal nerve courses alongside the nose to surface to the skin just on either side of the bridge of the nose. The vagus nerve leads from the brain (not shown) through the head and neck and into the thoracic cavity. General visceral efferent fibers extend from the vagus nerve and surface in the heart to control the heart and its pulse-rate. The trigeminal nerve, vagus nerve and general visceral efferent fibers serve as the autonomic pathway through which the dive reflex is activated, as depicted in FIG. 3. It can be seen that the trigeminal receptors and the telereceptors act on the cortical and hypothalamic centers which in turn act on the respiratory, the cardio (acceleratory and inhibitory centers), and the vasomotor centers.

When a triggering stimulus is applied to at least a portion of area in which the trigeminal nerve surfaces, the parasympathetic nervous system is triggered and slows the heartbeat by communicating with heart through the vagus nerve, and general visceral efferent fibers. Maximum heartbeat reduction is estimated to be 60 percent. The parasympathetic nervous system also causes vasoconstriction and its associated reduction in circulation to those body extremities and other organs thus extending anaerobic capability. Accordingly, the dive reflex can be selectively induced by applying a carefully controlled triggering source to the ophthalmic area depicted.

Figure 4:
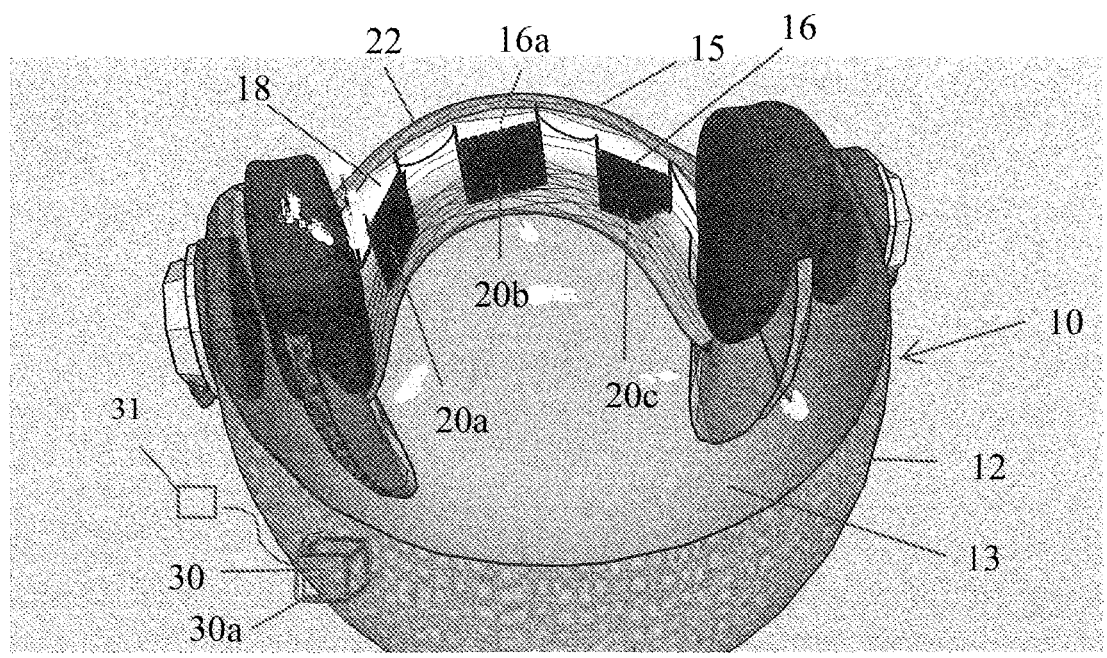
FIG. 4 is a view of the underside of a device helmet incorporating a plurality of stimulus components operable to stimulate the dive reflex in a person.
Figure 6:
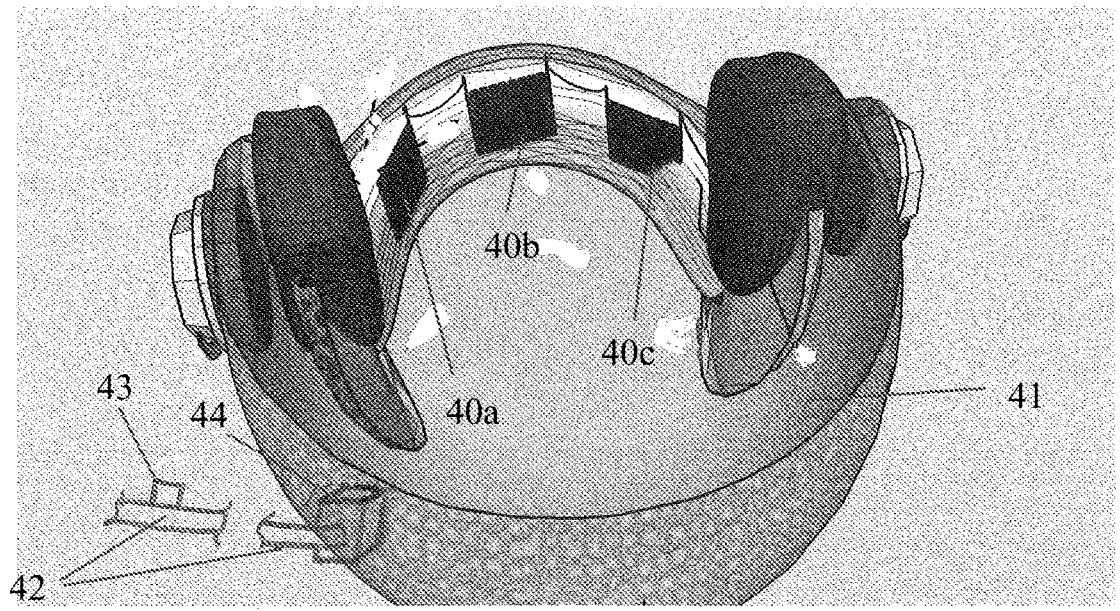
FIG. 6 is a view of the underside of a device helmet incorporating a plurality of stimulus components in the form of radiator cooling elements for use by an aviator.

According to one aspect of the present invention, a device 10 is provided for inducing the dive reflex in the person, as illustrated FIG. 4. In accordance with this embodiment, the device 10 includes a head gear component 12 that is configured to be worn by the person. The head gear component can include a helmet 13, as shown, or may incorporate other structure adapted to be worn by the person. The head gear component includes a face-engaging plate 15 that is arranged to encompass the ophthalmic zone of the trigeminal nerve of the person, particularly at a location where the trigeminal nerve approaches the surface of the skin, and more particularly to be in proximity to the location of the anterior ethmoidal nerve. In the illustrated embodiment, the face-engaging plate is in the form of a bar that is adjustably mounted to the helmet 13 so that the interior surface 16 of the bar can bear against the skin of the person. The interior of the bar 15 is provided with padding 18 for the comfort of the person. In lieu of a helmet, the device may have a structure similar to a conventional CPAP mask in which the mask is replaced with the face-engaging bar 15. It is contemplated that the head gear component 12 and particularly the face-engaging bar 15, may be formed of a moldable material that can be shaped to tightly conform to the anatomy of the person's face, and particularly to provide a snug fit on the bridge of the person's nose where the relevant branches of the trigeminal nerve are found.

The device 10 further includes a mechanism for stimulating the ethmoidal nerve in the form of a plurality of stimulus components 20a-c embedded within the padding 18 but near the interior surface 16 to maximize the effect of the stimulus produced by the components 20a-c. The stimulus components may be integrated into the padding or may be placed in pockets 16a formed in the padding to permit ready removal and replacement of the stimulus components. The plurality of components 20 are distributed on the face-engaging bar 15 so that a component is positioned in immediate proximity to a branch of the trigeminal nerve. For instance, in the embodiment shown in FIG. 4, three components 20 are provided, with two components 20a, 20b positioned on either side of the person's nose in immediate proximity to the anterior ethmoidal nerve and a third component 20c centrally located in proximity to the infracochlear nerve.

Figure 5:
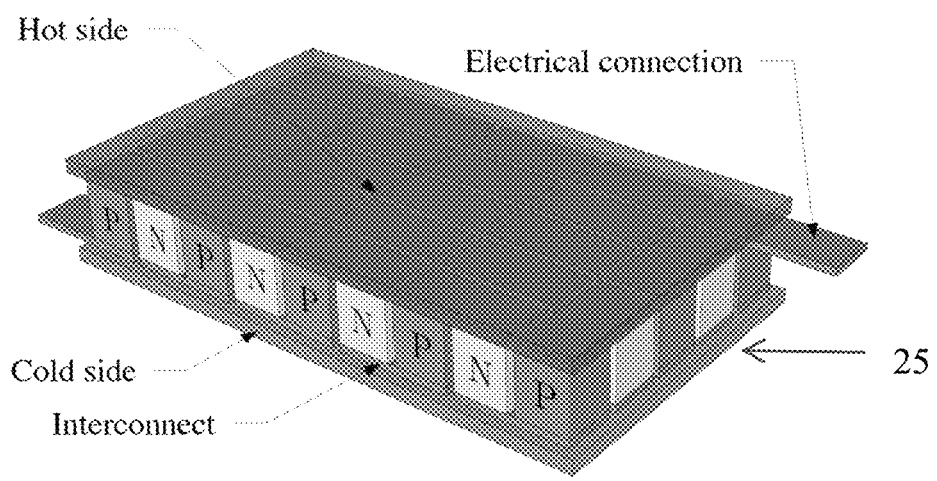
FIG. 5 is a perspective view of a Peltier device for use with the device shown in FIG. 4.

The stimulus components 20a-c are devices operable to simulate the application of cold water to the person's face. Thus, in one specific embodiment, the components 20a-c are thermoelectric cooling (TEC) devices, such as the Peltier device 25 shown in FIG. 5. As known in the art, a typical Peltier device includes two unique semiconductors with different electron densities. The semiconductors are placed thermally in parallel to each other and electrically in series and then joined with a thermally conducting plate on each side. When a voltage is applied to the free ends of the two semiconductors there is a flow of DC current across the junction of the semiconductors causing a temperature difference. The side with the cooling plate absorbs heat which is then moved to a heat sink on the other side of the device. The device 10, and particularly the face-engaging bar 15, includes a heat sink panel 22 that serves as the heat sink for the Peltier devices 20a-c. The heat sink panel 22 is operable to draw heat away from the Peltier devices and convey the heat to other parts of the headgear component 12. A Peltier device, such as device 25, is suitable for use as the stimulus components 20a-c because the can be provided in a minimal envelop, typically having a thickness of 15-25 mil.

The device 10 further includes a controller 30 that can incorporate a power supply or a mating connector for engagement to an external power supply. The controller 30 includes circuitry and electronics to control the activation of the stimulus components 20a-c. The controller 30 may thus be application specific, meaning that the manner and degree of control of the stimulus components depends upon the purpose of invoking the dive reflex in the person. For instance, if the device 10 is to be used as part of a pain management, palliative care or critical care regimen, the controller 30 can require manual external activation and de-activation. The controller 30 may include condition sensors 31, such as dermal temperature or heart rate sensors, to provide further control of the activation and de-activation of the stimulus components. For instance, the controller can be operable to de-activate the stimulus components when the skin temperature drops to a pre-determine temperature. Other sensors, such as bio-sensors like cardiac and brain wave monitors, may provide signals to the controller and the controller may incorporate appropriate electronics and/or software to control the operation of the stimulus components. The stimulus components 20a-c and the controller 30 may be configured to produce and maintain a temperature in a range of approximately 35° to 60° F. for a desired time period.

Another application of the device 10 is to offset the effect of G-forces on an aviator. With this application, the controller 30 may be configured to interface with the avionics on an aircraft allowing for synchronized activation of the stimulus components 20a-c upon receipt of information that a pre-determined level of G-forces are being applied. When the G-forces fall below the pre-determined level the controller 30 can deactivate the stimulus components. It can be appreciated that the activation of the diving reflex during high G-force maneuvers would help the aviator better tolerate the G-forces without losing consciousness or suffering from reduced awareness. In this particular application, the headgear component 12 can be the aviator's standard helmet with the stimulus components 20a-c and controller 30 integrated into the helmet. In this embodiment, the controller 30 may be driven by the avionics, as described, and/or may require manual activation of the aviator. In this latter case, the stimulus components may be activated by the aviator to provide cooling to the aviator's head.

The controller 30 on-board the device 10 may incorporate the power supply, such as power supply 30a, or power supply access and may itself have limited functionality. In this embodiment, the controller 30 includes a component for communication with an external controller. The component may be an electrical input for a hard-wired connection to an external device, such as a laptop computer. Alternatively, the component may be operable to provide a wireless communication link with the external device, such as an IR, Bluetooth™ or wireless communication link. The external device could be a "smart" device, such as a smart phone or smart pad, which operates a software app to control the operation of the controller 30 and ultimately the stimulus components 20a-c. The software or app executed by the external device can be tailored to the specific application for invoking the dive reflex response.

The present invention contemplates other forms of stimulus components that are capable of stimulating the trigeminal nerve to invoke the dive reflex response. In one embodiment, stimulus components 40a-c may be in the form of radiator elements mounted in a helmet 41 that are connected to an external source of cool or cold air. In an aircraft, the external source can be ambient air diverted through a pitot tube outside the aircraft into a delivery hose 42 inside the aircraft for connection to the device 10. The delivery hose 42 may incorporate a heating element 43 to warm the incoming ambient air (which can be 20-30° F. below zero) prior to introduction into the stimulus components 40a-c. Cold air flow through the delivery hose 42 into the radiator elements 40a-c provide convection cooling to the person at the trigeminal nerve to stimulate the dive reflex. In this embodiment, a controller 44 is provided that controls a flow regulator valve integrated into the helmet 13 or into the controller, with the nature of the control depending on whether the need for dive reflex stimulation is indicated or whether the device 10 is being used simply as a cooler for the aviator. The controller 44 may also be configured to control the heating element 43, particularly when the stimulus components are being used by the aviator as an internal cooling system. The delivery hose may incorporate a discharge hose or the helmet 41 may be provided with vents to vent the air stream outside or inside the helmet.

In the above embodiments, the trigeminal nerve is stimulated by the application of extreme cold to the person's face, thereby activating the nerve and the dive response. In an alternative approach, the trigeminal nerve may be directly stimulated by application of a small electrical current to the surface of the skin. With this approach, the stimulus components 20a-c described above are replaced with an electrical stimulus device that is held in direct contact with the person's skin at the location of the trigeminal nerve branches of interest. The electrical stimulus devices can be TENS units (Transcutaneous Electrical Nerve Stimulators), Micro-TENS units, pulsed galvanic stimulators, interferential stimulators, or muscle stimulators. In this embodiment, the controller 30 may include a power supply and a controllable transformer to power the electrical stimulus devices. The controller 30 may be operable at several settings to control the electrical current provided to the electrical stimulus devices to achieve a maximal or desired result.

As a further alternative, the electrical stimulus components may be self-powered, meaning that a separate power supply is not required. In this alternative, the electrical stimulus components may be in the form of a battery cell that is activated when desired. The battery cell may be a chemical battery embedded into a conductive patch supported by the head gear component, such as component 12. A controller, such as the controller 30, is operable to activate the battery cell which then generates an electrical signal applied to the skin through the conductive patch to thereby activate the trigeminal nerve.

Figure 7:
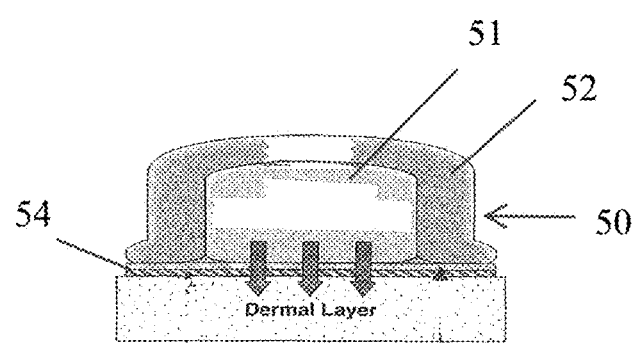
FIG. 7 is a cross-sectional representation of a patch including stimulus components for triggering the dive reflex in a person upon application of the patch.

As described above, the face-engaging padding 18 may be provided with pockets for holding the stimulus components 20a-c. In a further embodiment, the stimulus components may be activated independently of the device 10 and then placed in a corresponding pocket. The user dons the head gear component 12 so that the stimulus components are in contact with the use's face, as described above. In this embodiment, the stimulus components are patches, such as patch 50 show in FIG. 7, that contain a composition that operates as a cold receptor agonist capable of stimulating the dive reflex. The composition may be a salve, lotion, cream or emollient, or other flowable composition. The patch 50 includes a body 52 that defines a reservoir 51 for the composition. The reservoir 51 communicates with a permeable membrane 54 that is held in contact with the use's skin by the face-engaging padding 18. The patch 50 may be provided with a releasable liner (not shown) initially covering the permeable membrane 54. For use, the liner is removed, the patches 50 are placed within the pockets in the face-engaging padding 18 at the positions 20a-c (FIG. 4) and the head gear component is placed on the user's head. The composition immediately flows through the membrane into contact with the skin, thereby prompting a reaction of the trigeminal nerve and invocation of the dive reflex. The salve, lotion, cream or emollient can be menthol, menthol derivative, menthol receptor agonists (linalool, geraniol, hydroxycitronellal, WS-3, WS-23, FrescolatMGA, FrescolatML, PMD38, CoolactP and Cooling Agent 10), or other cold receptor agonists.

In an alternative, the salve or lotion within the patch 50 may be an activatable composition including at least two substances initially contained within separate reservoirs in the patch. The composition is activated by rupturing a wall between the two compartments, thereby allowing the substances to mix. Upon mixing, the composition produces an endothermic reaction reducing the temperature of the patch and thus the dermal interface to a desired temperature that is sufficient to initiate the dive reflex, such as 35-40° F. Two suitable components are urea and water, which in a 50:50 mixture will reduce the patch temperature to about 35° F. for about three hours. Different temperatures and durations can be obtained with different ratios of urea and water. It can be appreciated that in this alternative embodiment the stimulus components are single use, meaning that once the composition has been activated to create the endothermic reaction the reaction will continue unabated until the chemical reaction is complete, after which the composition is inert.

In this alternative as just described, the patch 50 is held within pockets in the head gear component 12. Alternatively, the patch 50, and particularly the body 52, may be formed in a shape to conform to the bridge of a person's nose. The body 52 may also be slightly moldable from this initial conforming shape so that the body can be precisely molded to the particular user's anatomy. The body 52 around the permeable membrane or the permeable membrane 54 can be provided with an adherent or tacky layer that is adapted for removable adhesion to a person's skin. Suitable tacky layers can include hydrocolloid adhesives, acrylate adhesives, polybutene, resin tackifiers or other known material. As a modification of the steps described above, once the internal components have been activated to initiate the endothermic reaction, the body 52 of the patch 50 is pressed onto the bridge of the user's nose. The patch can be readily removed once the reaction is complete or as desired by the user. It can be appreciated that the salve/lotion embodiment discussed above could also be implemented in a similar manner.

In a further aspect of the invention, a method is provided for improving the outcome of a soldier or patient in the setting of shock, impending shock, fainting, or profound blood loss. Historically, MAST (military anti shock trousers) have been utilized with the intent to increase the systemic vascular resistance of the wearer to afford them greater protection against drops in blood pressure or shifts of blood away from the center axis of the brain and heart. Unfortunately, these devices fell out of favor in the 1990's due to their inability to actually sustain any increase in SVR (systemic vascular resistance). As the MAST was inflated approximately 900 ccs of blood was pushed into the central circulation and the strike volume of the heart increased.

Counter-regulatory actions of the heart provide for the reflex mechanism of a drop in SVR to counter the sudden increased stroke volume and the intended benefit was quickly lost. The triggering of the dive reflex affords a mechanism whereby the entire autonomic nervous system works together to create an increase in SVR (on the order of 25%) with a secondary drop in cardiac work and a surprising increase in cerebral blood flow. The present invention provides a device capable of triggering the dive reflex on demand, which can get an injured or bleeding soldier through the so-called "Golden Hour" where he/she needs to be transferred to acute care before death or irreversible injury occurs. Even in the field, a soldier who just sustained a round or shrapnel to a vein or artery may be able to activate the present device to trigger the dive reflex thereby staying conscious long enough to fend off further attacks or to signal for help. Even the setting where a bullet may have impaled a major internal structure such as the liver or even the spleen, would be benefited by triggering the dive reflex where the spleen is known to contract by as much as 20% upon activating the dive reflex and the hematocrit or blood volume may go up as much as 10% upon contracture of the spleen. Oxygen carrying capacity to vital organs is not only preserved but may actually be increased to the critical organs of heart and brain at this life threatening juncture. In accordance with this aspect of the invention, the soldier's helmet is equipped in the manner of the helmet 10 described above. The controller 30 may be equipped with a manually activatable switch that allows the soldier to activate the stimulus components 20*a-c* in the event of a trauma. Alternatively, the controller 30 may be equipped with sensors that continuously monitor the soldier's vital signs and is calibrated to automatically activate the stimulus components when the vital signs signal the onset of a trauma.

In a further aspect, the device and method of the present invention can be implemented to trigger the dive reflex in a person with the intent to improve the oxygen supply/demand curve to the heart or brain. The 100-year-old sublingual nitroglycerine tablet works by a very simple and well defined mechanism. The nitroglycerine is absorbed through the oral mucosa and circulates to the endothelial lining of the arteries and veins of the system. In the vessel lining, the nitroglycerin is converted to nitric oxide, a known vasodilator. The venous system is actually dilated greater than the arterial system (which is generally not an advantageous), but the reduced flow into the heart (by dilating the veins) appears to reduce oxygen demand by the heart so that the risk of angina or congestive heart failure is reduced. Activation of the dive reflex in the person can impart an even greater theoretical benefit to the vascular tree, especially to the heart and brain. Just as in the sublingual nitroglycerine, the oxygen demand (cardiac work) has been demonstrated to drop by more than 10%. Moreover, unlike nitroglycerine, the dive reflex shunts oxygen rich blood away from non-essential peripheral organs back to the heart and brain. Further, the dive reflex has been demonstrated to actually increase cerebral blood flow, which has not shown in the use of nitroglycerine. The spleen has been shown to contract upon triggering the dive response which serves to increase the hematocrit (volume of blood) to bolster the oxygen carrying capacity of the blood stream thereby benefiting the heart and brain. Nitroglycerine has been known to cause an unfavorable reflexive increase in heart rate (tachyphylaxis) that is injurious to the oxygen starved heart. On the other hand, the dive reflex causes bradycardia (20-70% drop) which is generally preferable to the tachyphylaxis caused by nitroglycerine. Furthermore, sublingual nitroglycerine is known to take 2-4 minutes to act, last only 25-30 minutes, often result in tolerance to the drug, and often result in severe headaches. The triggering of the dive reflex would not be expected to result in any of these side effects. Thus, in accordance with this method of the invention, a person in need of increased oxygen supply to the heart and brain is fitted with a helmet, such as the helmet 10, and the stimulus components 20*a-c* are activated to produce the dive reflex response in the person. A less intrusive head gear component, such as the CPAP-type component described above, may be used, or an individually applied patch, such as the patch 50 may be used.

In a similar manner the devices disclosed herein can be used to trigger the dive reflex in a person with the intent to mitigate or prevent migraine headaches. Migraines are known to be caused by a spasm of the cerebral vessels with resulting vasodilatation leading to pain thereafter. If the patient were able to trigger the dive reflex immediately upon recognizing the premonitory signs (visual symptoms, tunnel vision, altered taste, smell, numbness for example), then they may be able to abort the headache before it starts. The person may don a helmet, such as the helmet 10 shown in FIG. 4, or a less obtrusive head gear component 12, such as the CPAP mask-type component. Alternatively, the person may apply the patch 50 shown in FIG. 7.

The devices disclosed herein may further be used to initiate the dive reflex with the intent to improve the medical condition known as brain attacks also known as strokes, RINDS (reversible ischemic neurological deficits) or TIAS (transient ischemic attacks). Certainly, there may be a contraindication to triggering the dive reflex if a neurological event were to be secondary to a hemorrhagic event. Further, since it may not be obvious whether an event is hemorrhagic or not, an imaging procedure may be required before initiating the dive reflex in the stated setting. Similarly, the dive reflex can be triggered with the intent to improve the hypotension associated with medical conditions such as Shy-Dragar's Syndrome, Holmes-Adie syndrome, autonomic neuropathy from diabetes or any cause, orthostatic hypotension from drugs or prior strokes, or from any hypotensive cause. In these settings the dive reflex can be triggered on demand to allow the individual a temporary reprieve from the orthostatic drop in blood pressure experienced. As with the previously-described methods, any of the devices disclosed herein may be implemented to activate the dive reflex in the patient.

The present disclosure should be considered as illustrative and not restrictive in character. It is understood that only certain embodiments have been presented and that all changes, modifications and further applications that come within the spirit of the disclosure are desired to be protected. For instance, the devices and methods described herein may be used to trigger the dive reflex response in a person to address any of the following medical conditions, as well as other similar conditions:

(a) to improve the blood flow to the brain during a fainting spell, migraine headache attack, cluster headache attack, panic attacks, or even a seizure;

(b) to improve the outcome of brain surgery or cardiothoracic surgery outcomes;

(c) to improve known hypotensive conditions such as Shy-Dragar's Syndrome, Holmes-Adie syndrome, autonomic neuropathy from diabetes or any cause, orthostatic hypotension from drugs or prior strokes, or from any cause;

(d) to improve any tachycardia rhythm of the heart or even convert supraventricular tachycardia (SVT) or paroxysmal SVT to normal sinus rhythm when it occurs as an outpatient or when the patient presents to the Emergency Medical System (EMT, Paramedic, Medic, or Emergency Room). Such rhythms include but are not limited to atrial fibrillation, Wolf-Parkinson-White Syndrome (WPW), AVNRT (AV nodal reentrant tachycardia), AVRT (AV reentrant tachycardia), or Junctional Tachycardia;

(e) to improve cardiac and cerebral outcomes after any surgery where anesthesia is administered. Anesthesia can lead to carotid baroreceptor dysfunction that could be benefited by the dive reflex;

(f) to improve survival technique when one is lost in the snow, lake or ocean water, or even just wilderness exposure waiting to be found. Extending the victim's survival time would improve the likelihood of search teams locating the victim;

(g) to improve the tolerance of hypoxia (lack of oxygen) during sleep apnea or other altered sleeping patterns. Sleep apnea is known to adversely alter the autonomic nervous system and even trigger high blood pressure in more than half of patients with the disorder. Reducing cardiac demand and oxygen consumption would benefit the individual greatly. Use, in conjunction with CPAP (Continuous Positive Airway Pressure), would further augment the actions of the dive response as triggering mechanoreceptors in the lungs (such as with breath holding) has shown even greater dive response activation;

(h) to improve a palpitations condition whereby the heart is summoned to beat too early in its cycle and the dive reflex could slow, stop or prevent such an action.

What is claimed is:

1. A device for inducing the drive reflex in a person, the person having a head with a face, nose, skin and a trigeminal nerve, comprising:
   at least one electrical stimulus component operable to stimulate a branch of the trigeminal nerve of the person in a manner sufficient to induce a drive reflex response in the person;
   an electrical controller associated with an electrical power supply operably connected to the at least one stimulus component to delivery stimulation, wherein the stimulation is configured to stimulate the branch of the trigeminal nerve of the person only in a manner sufficient to induce the drive reflex response in the person; and
   an apparatus for supporting the controller and for supporting the at least one stimulus component in contact with the person's face directly adjacent the branch of the trigeminal nerve.

2. The device of claim 1, wherein the apparatus includes a head gear component adapted to be worn on the head of the person and including a face-engaging plate supporting the at least one stimulus component in direct contact with the face of the person directly adjacent the branch of the trigeminal nerve.

3. The device of claim 1, wherein:
   the at least one stimulating component includes a Peltier device operable to reduce the temperature of the person's skin when in contact with the person's face directly adjacent a branch of the trigeminal nerve; and
   said controller includes a power supply for providing electrical power to the Peltier device.

4. The device of claim 1, wherein:
   the at least one stimulus component is controllable to maintain a predetermined temperature of the person's skin when in contact with the person's face; and
   the controller is configured to control the at least one stimulus apparatus to maintain the predetermined temperature.

5. The device of claim 4, wherein the at least one stimulus component is operable to maintain a temperature in the range of 35-60° F.

6. The device of claim 1, wherein the controller is connected to one or more sensors configured to sense a physiological or ambient condition of the person and is operable to activate the at least one stimulus component when a sensed condition is outside a threshold value.

7. The device of claim 6, wherein the ambient condition is a G-force experienced by the person and the threshold value is a G-force value at which the person experiences reduced awareness or loss of consciousness.

8. The device of claim 6, wherein the controller is configured to de-activate the at least one stimulus component when a sensed condition is within a threshold value.

9. The device of claim 1, wherein the at least one stimulus component includes a component for applying an electrical current to the person's face.

10. The device of claim 9, wherein the component is a transcutaneous electrical nerve stimulator (TENS) device.

11. A device for inducing the drive reflex in a person, the person having a head with a face, nose, skin and a trigeminal nerve, comprising:
    at least one stimulus component to deliver stimulation to stimulate a branch of the trigeminal nerve of the person, wherein the stimulation is configured to be sufficient to induce a drive reflex response in the person; and
    an apparatus for supporting the at least one stimulus component in contact with the person's face directly adjacent the branch of the trigeminal nerve, wherein the apparatus is a patch configured to conform to the person's face about the nose in proximity to the branch of the trigeminal nerve of the person, the patch including;
    a body defining a reservoir;
    a permeable membrane; and
    an adherent layer adapted to removably adhere to the skin of the person; and
    the at least one stimulus component includes a composition adapted to pass through the permeable membrane into contact with the person's skin and is adapted to stimulate the trigeminal nerve to activate the drive reflex in the person.

12. The device of claim 11, in which the head of the person has an anterior ethmoidal nerve, wherein the patch is configured to conform to the person's face about a bridge of the nose in proximity to the anterior ethmoidal nerve of the person.

13. The device of claim 11, wherein the composition is a cold receptor agonist.

14. The device of claim 13, wherein the composition includes menthol, a menthol derivative or a menthol receptor agonist, such as linalool, geraniol, hydroxycitronellal, WS-3, WS-23, FrescolatMGA, FrescolatML, PMD38, CoolactP and Cooling Agent 10.

15. A device for inducing the drive reflex in a person, the person having a head with a face, nose, skin and a trigeminal nerve, comprising:
    at least one stimulus component to deliver stimulation to a branch of the trigeminal nerve of the person, wherein the stimulation is sufficient to induce a drive reflex response in the person; and an apparatus for supporting the at least one stimulus component in contact with the person's face directly adjacent the branch of the trigeminal nerve, wherein each of the at least one stimulating component includes a Peltier device operable to reduce a temperature of the person's skin when in contact with the person's face directly adjacent the branch of the trigeminal nerve.

16. The device of claim 15, wherein the apparatus includes a head gear component adapted to be worn on the head of the person and including a face-engaging plate defining at least one pocket configured to receive a corresponding one of the at least one stimulus component in direct contact with the face of the person directly adjacent the branch of the trigeminal nerve.

17. The device of claim 16, wherein the face-engaging plate includes a heat sink panel in contact with each Peltier device of each of the at least one stimulus component on a surface of the Peltier device opposite the skin of the person.

* * * * *